United States Patent [19]

Crowley et al.

[11] Patent Number: 4,951,677
[45] Date of Patent: Aug. 28, 1990

[54] ACOUSTIC IMAGING CATHETER AND THE LIKE

[75] Inventors: Robert J. Crowley, Wayland; Lucien A. Couvillon, Jr.; John E. Abele, both of Concord, all of Mass.

[73] Assignee: Prutech Research and Development Partnership II, San Jose, Calif.

[21] Appl. No.: 171,039

[22] Filed: Mar. 21, 1988

[51] Int. Cl.$^5$ .............................................. A61B 8/12
[52] U.S. Cl. .................................. 128/662.06; 128/4
[58] Field of Search .............................. 128/660–663; 73/861.25, 623

[56] References Cited

U.S. PATENT DOCUMENTS

| | | | |
|---|---|---|---|
| 4,466,444 | 8/1984 | Baba | 128/662.06 |
| 4,821,731 | 4/1989 | Martinelli et al. | 128/662.06 |
| 4,841,977 | 6/1989 | Griffith et al. | 128/660.03 |

OTHER PUBLICATIONS

Yock, P. G., "Catheter Apparatus", EP0234951 (Europ. Patent Appln) Publ. 02-09-87.

*Primary Examiner*—Francis Jaworski
*Attorney, Agent, or Firm*—Fish & Richardson

[57] ABSTRACT

Acoustic imaging catheters formed by a disposable liquid-confining sheath supporting a high fidelity, flexible drive shaft which carries on its end an ultrasound transducer. The shaft and transducer rotate with sufficient speed and fidelity to produce real time images on a T.V. screen. Special features that contribute to the high fidelity of the drive shaft include the particular multifilar construction of concentric, oppositely wound, interfering coils, a preloaded torque condition on the coils enhancing their interfering contact, and dynamic loading of the distal end of the probe, preferably with viscous drag. The coil rotating in the presence of liquid in the sheath is used to produce a desirable pressure in the region of the transducer. Numerous selectable catheter sheaths are shown including a sheath with an integral acoustically-transparent window, sheaths with end extensions that aid in positioning, a liquid injection-producing sheath, a sheath having its window section under tension employing an axially loaded bearing, a sheath carrying a dilatation or positioning balloon over the transducer, a sheath carrying a distal rotating surgical tool and a sheath used in conjunction with a side-viewing trocar.

50 Claims, 12 Drawing Sheets

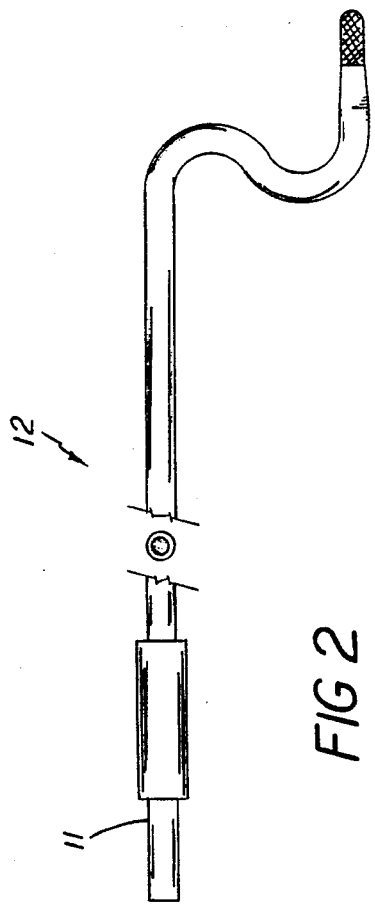
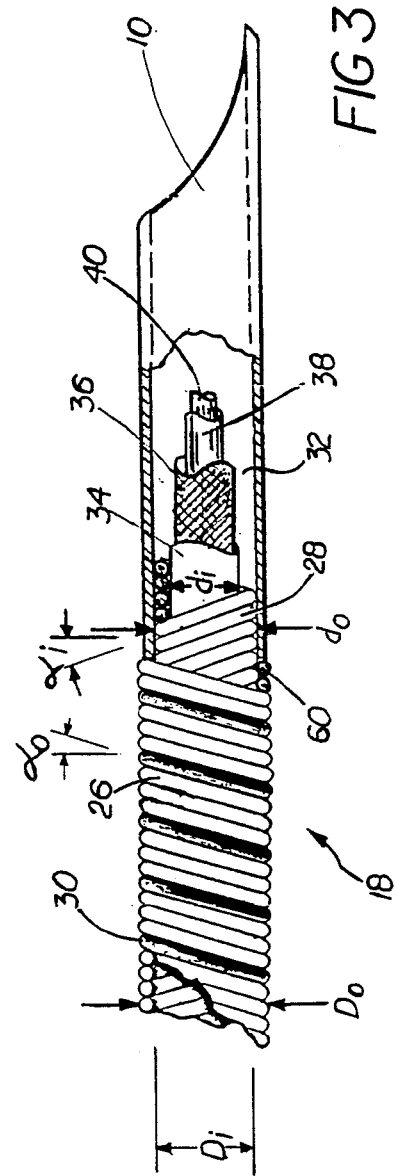

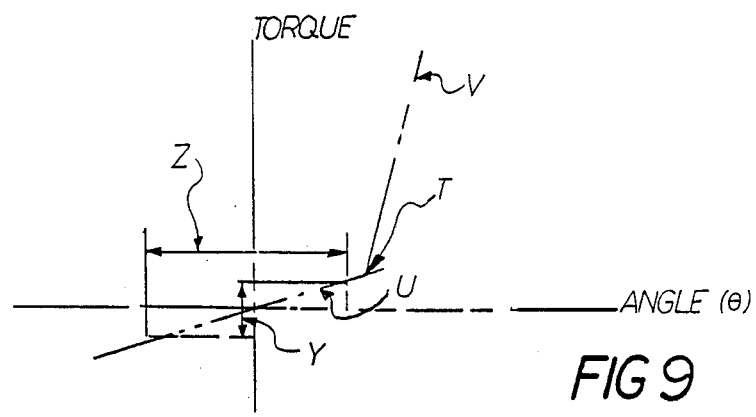
FIG 9
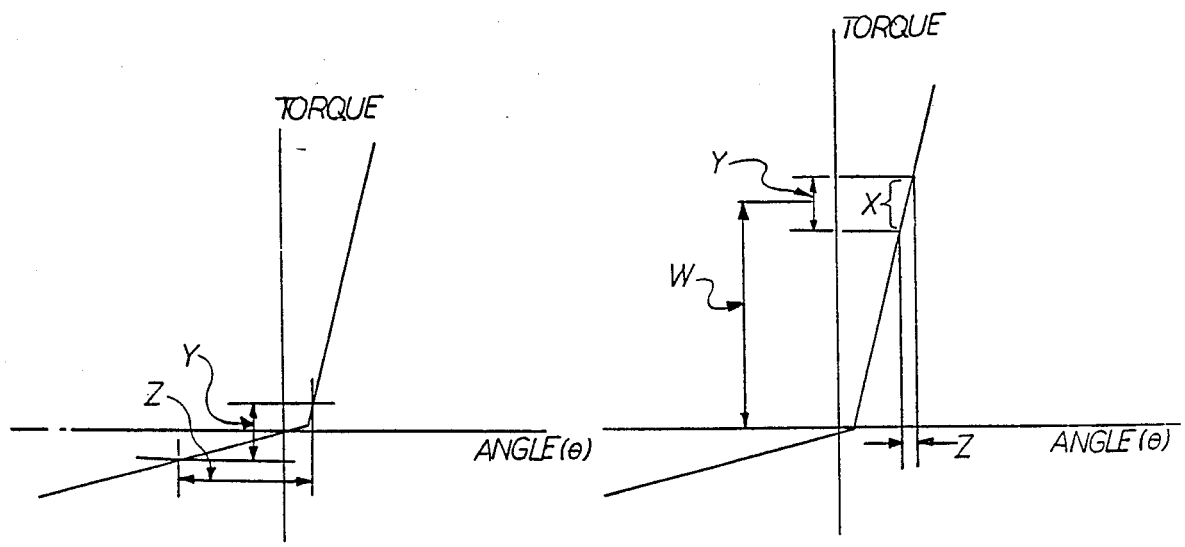
FIG 10
FIG 11
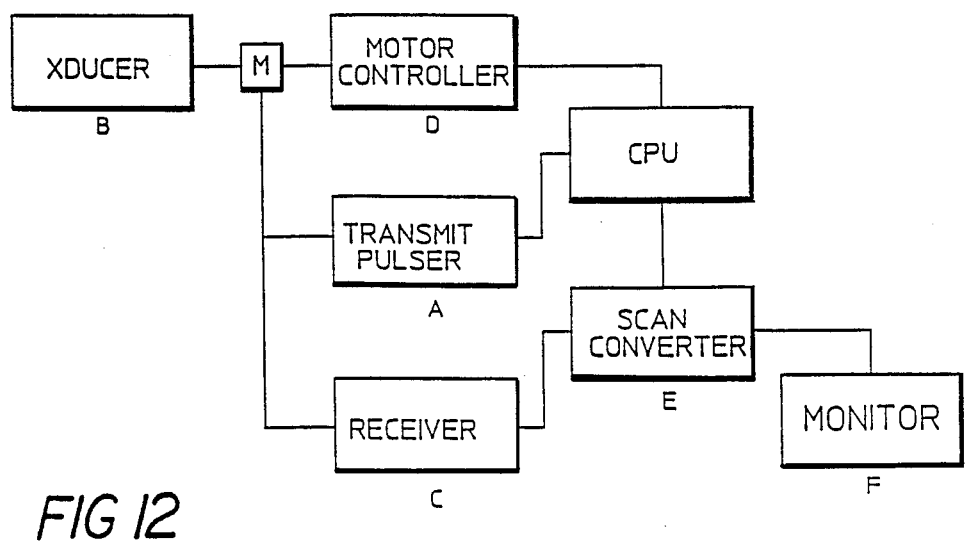
FIG 12

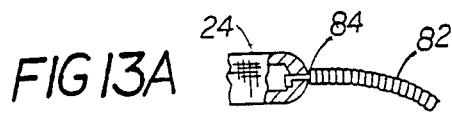
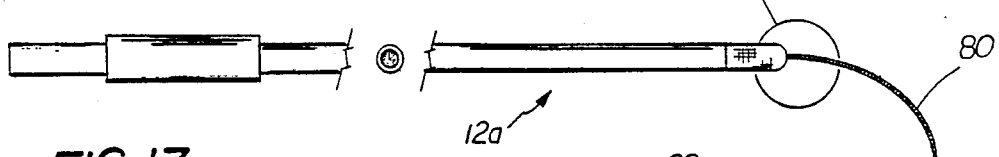
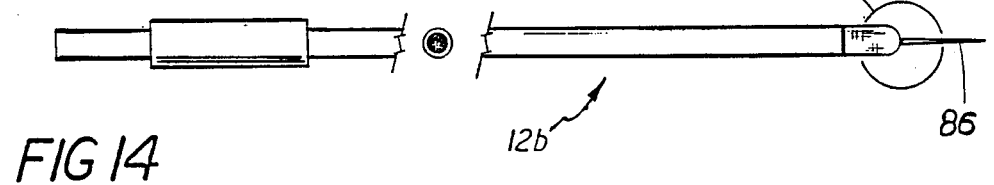
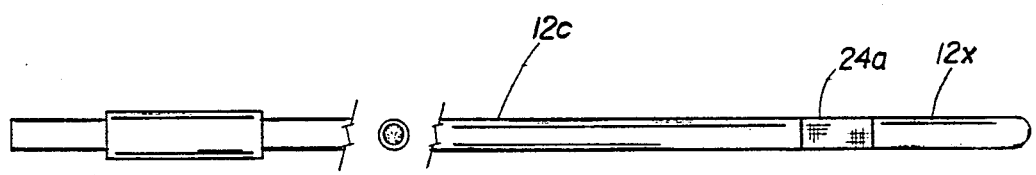
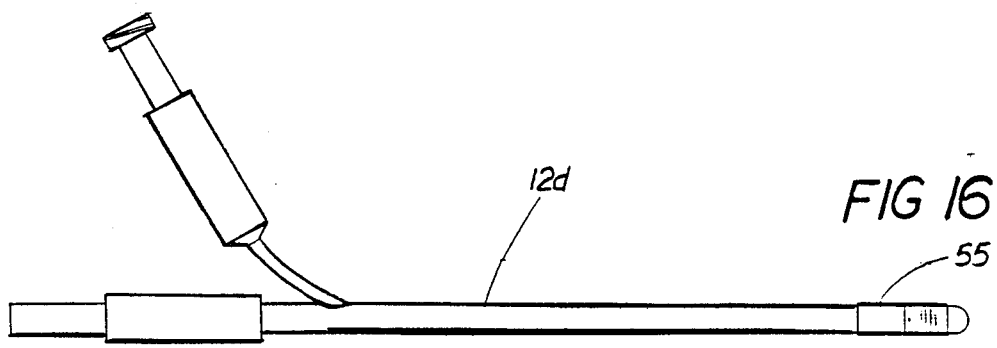
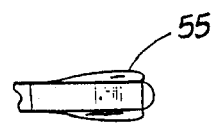
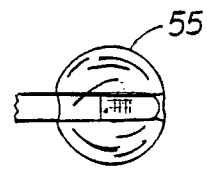

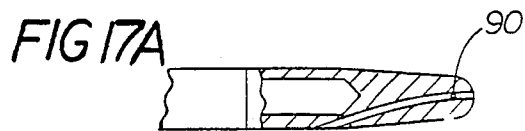
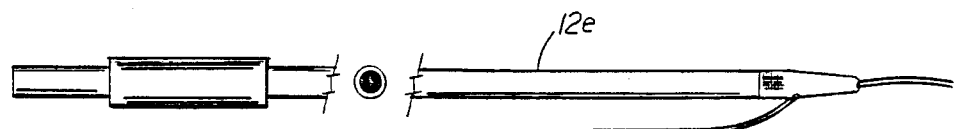
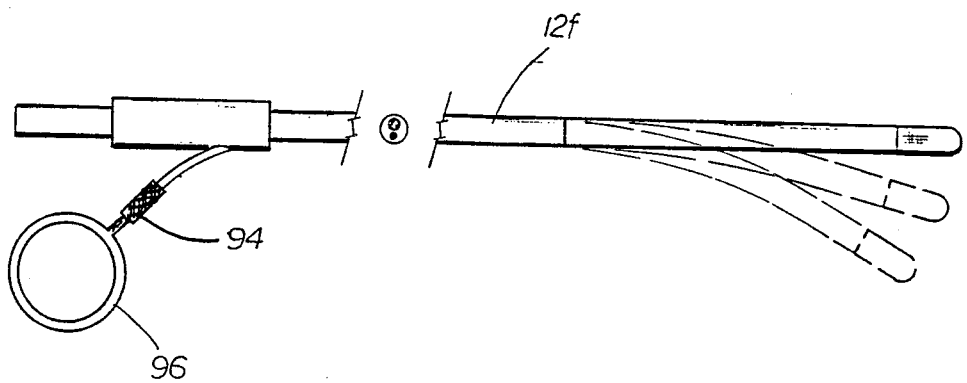

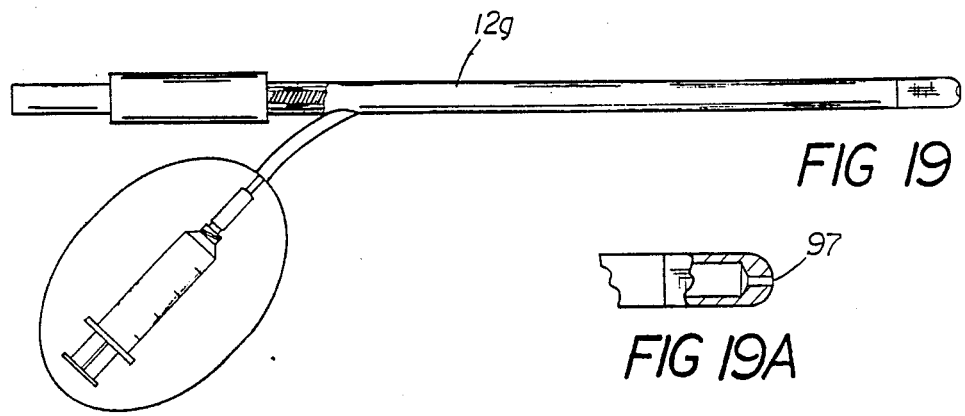
FIG 19
FIG 19A
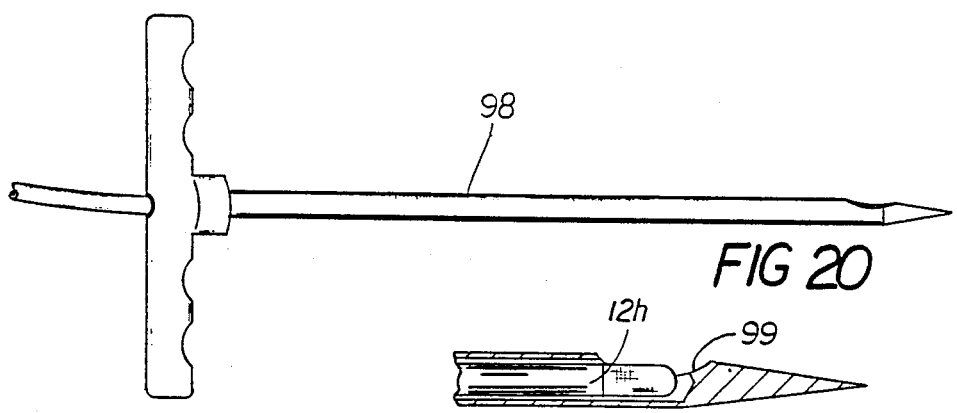
FIG 20
FIG 20A
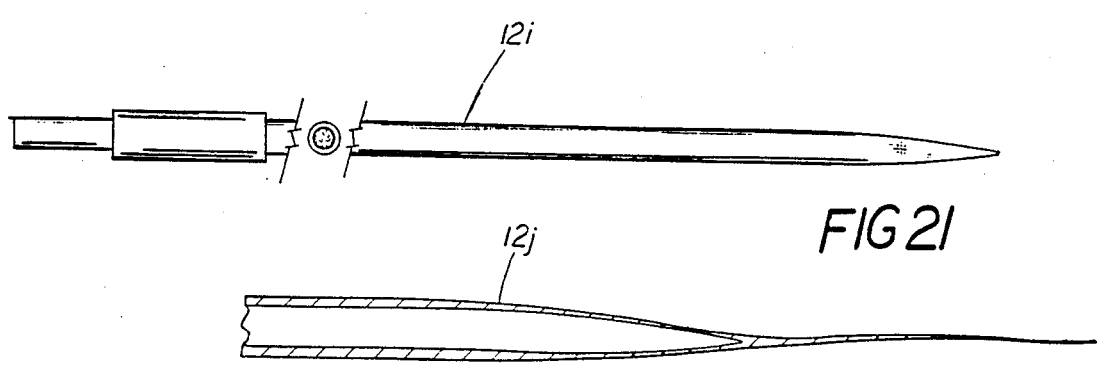
FIG 21
FIG 22

ACOUSTIC IMAGING CATHETER AND THE LIKE

BACKGROUND OF THE INVENTION

This invention relates to acoustic imaging catheters employing a rotating transducer.

It has long been recognized that acoustic imaging by use of internal probes has potential use in visualizing conditions of a body.

For example, Brown et al., U.S. Pat. No. 2,949,910, describes a catheter within a heart which detects heart size by a fixed transducer which emits sound waves and detects the echo return; Bom, U.S. Pat. No. 3,938,502, describes an ultrasonic device to be placed within a heart, comprising a catheter of 3 mm outer diameter having a plurality of fixed transducers. Peronneau, U.S. Pat. No. 3,542,014, describes a catheter having a piezoelectric transducer for measuring the size of a blood vessel; Frazer, U.S. Pat. No. 4,176,662, describes an endoscope employing a transmitter of ultrasonic energy waves so that its position within a body can be determined; Green et al., U.S. Pat. No. 4,327,738, describe an endoscope, having a transducer which is inserted into a body cavity such the stomach; Trimmer et al., U.S. Pat. No. 4,431,006, and Leeny et al., UKA 2,175,828, describe solid needles, for detecting sound waves, which may be inserted within a body; Silverstein et al., U.S. Pat. No. 4,462,408, describe an endoscope having an array of ultrasonic transducers which can be inserted into a body cavity such, as the stomach; and Pourcelot et al., U.S. Pat. No. 4,605,009, describe an endoscopic probe suitable for studying coronary arteries. Other internal probes have been proposed which cause movement of the ultrasonic beam to produce images of body features, of which the following are examples.

Eggleton et al., U.S. Pat. No. 3,779,234, describes an ultrasonic catheter for placement through an esophagus or chest wall. The catheter rotates at 360 rpm and has four transducers each having a diameter of 5 mm. The transducers are focused horizontally with an effective depth of penetration of about 15 cm. The housing of the catheter rotates and "may be a flexible stainless steel shaft constructed of right and left helices to maximize the torsional stiffness of the rotating assembly with the stationary housing. [such as produced by S. S. White and Company]".

Baba, U.S. Pat. No. 4,374,525, describes an ultrasonic device which may be placed within a body cavity and against a body wall. The transducers are rotated at between 500–900 rpm. The inserted section is generally rigid, but flexible enough to be placed against a body wall.

Suwaki et al., U.S. Pat. No. 4,375,818, describe an endoscope having an ultrasonic transducer suitable for positioning within a celiac cavity. The transducer can be rocked by a drive motor adjacent to it.

Ando et al., U.S. Pat. No. 4,391,282, describe an ultrasonic apparatus for celiac cavity insertion, for examination of the heart and pancreas. "[A] flexible power transmission member such as a coil wire or the like . . . " is provided.

Nakada et al., U.S. Pat. No. 4,558,706, describe an ultrasonic and optical device. The ultrasonic pulse is rotated by a mirror held on a "soft shaft formed of two inside and outside wound layer coils. These inside and outside coils are wound reversely to each other so that the outside diameter will not vary with the rotating direction and the rotation will be able to be effectively transmitted when curved." Gas bubbles generated within the catheter are removed through a conduit passing from the housing chamber to an outside chamber.

Kondo et al., U.S. Pat. No. 4,572,201, describe an intraluminal ultrasonic scanner which can be inserted into the stomach or pancreas The transducer is secured to a rotary shaft connected to a flexible shaft.

Andou et al., U.S. Pat. No. 4,674,515, describe an ultrasonic endoscope suitable for placement in a body cavity.

DE 3,619,195, appears to describe an ultrasonic catheter with a coil-spring driven magnet, which, by magnetic coupling, in turn causes rotation of a transducer.

Others previously have suggested employing miniature ultrasonic catheters to sense the wall thickness of blood vessels from within the vessel. Such suggestions have included rotatable catheters and sensing the rotation to provide so-called B-mode images of wall thickness.

Wider effective use of acoustic imaging would occur, especially in the vascular system, if such a system could be considerably smaller, have good image fidelity, and be simple, inexpensive and dependable.

SUMMARY OF THE INVENTION

According to one aspect of the invention, an elongated, flexible ultrasonic probe of the type comprising a coil-form drive shaft and an acoustic transducer carried on the distal end of the drive shaft, is provided wherein, (a) the drive shaft comprises at least a pair of inner and outer, concentric, oppositely and closely wound, hollow, multifilar coils, (b) each coil has a ratio of outer radius of coil to thickness of coil filament in the radial direction of between about 2½ and 10, (c) the coils are joined together at their respective ends with interfering contact with each other along their mutual length, and (d) the filaments of each coil have a pitch angle of about 20° or greater, so that when drive torque is applied to the drive shaft from the proximal end in the direction tending to reduce the diameter and lengthen the outer coil and increase the diameter and shorten the inner coil, a substantial component of the resultant stress on each filament of the coils is aligned with the axis of the filament, whereby substantial mechanical fidelity of angular displacement between the transducer and the proximal end of the drive shaft is maintained during rotation of the drive shaft.

According to another aspect of the invention an acoustic catheter is provided comprising an elongated, flexible, liquid-confining catheter sheath and an elongated, flexible ultrasonic probe disposed within and rotatably supported by a lumen of the sheath, the ultrasonic probe comprising a transducer supported on the end of an elongated coil-form drive shaft, the exterior of the drive shaft being supported by the internal surface of the catheter lumen, the inner diameter of the lumen being no more than about ¼ mm greater than the outer diameter of the drive shaft along most of their mutual length and being no more than about 1/10 mm greater than the outer diameter of the drive shaft in the distal region of the drive shaft and the transducer, a distal portion of the catheter sheath that corresponds with the position of the transducer being substantially transparent to acoustical energy trasmitted and received by the transducer and the probe and the sheath being cooperatively constructed and arranged to enable removal and replacement of the sheath in a disposable manner.

According to another aspect of the invention, there is provided a catheter sheath, per se, adapted to receive and rotatably support a predetermined elongated ultrasonic probe of the type comprising a coil-form rotatable drive shaft of predetermined length and an acoustic transducer carried on the distal end of the drive shaft, the path of rotation of the transducer having a diameter no greater than the drive shaft, the catheter sheath comprising a closed-end, elongated, flexible liquid-confining, resinous, flexible member having a lumen for receiving the probe, a distal portion of the sheath corresponding to the position of the rotatable transducer when inserted in the lumen being substantially transparent to acoustical energy transmitted and received by the transducer, the internal surface of the lumen sized to rotatably support the drive shaft.

The invention also features oppositely wound coils of a flexible acoustic probe drive shaft in torsionally prestressed condition in the direction causing the outer coil to bear radially in tight contact upon the inner coil. The invention also features means at the distal end of an acoustic probe drive shaft adapted to apply dynamic drag to the rotation of the flexible shaft to enhance the mechanical fidelity of angular displacement between the proximal and distal ends of the probe.

Preferred embodiments of the invention feature the drive shaft having an outer diameter throughout its length of about 1 mm or less; a liquid-filled, relatively fixed, first sheath portion closely surrounding a segment of the distal end of the drive shaft, adapted to apply dynamic, viscous drag to the shaft during its rotation, to enhance the mechanical fidelity of angular displacement between the proximal and distal ends of the probe; the difference between the outer diameter of the shaft segment and the inner diameter of the corresponding sheath portion being in the range of about 0.05 to 0.15 mm; a second sheath portion extends a substantial distance proximally from the first sheath portion, the second sheath portion being radially spaced a greater distance from the drive shaft than the radial spacing of the first sheath portion from said shaft segment; a continuous flexible resinous sheath, of which the first sheath portion is part, encloses the transducer and drive shaft, the portion of the sheath that corresponds with the position of the transducer being substantially transparent to acoustical energy transmitted and received by the transducer; the sheath comprises a catheter sheath having an outer diameter throughout its length of less than about 3 mm; the outer surface of the outer coil of the drive shaft has a liquid-pumping screw-form contour, whereby, when the drive shaft, while exposed to liquid in the sheath, is driven in the direction tending to decrease the diameter of the outer coil, the outer surface of the coil is effective to pressurize liquid distally thereof; there is fluid communication between the liquid-filled space along the drive shaft and the space occupied by the transducer, whereby the action of the screw-form contour of the shaft is effective to pressurize liquid in which the transducer is immersed; the sheath comprises a catheter sheath having a distal projection supported by the catheter sheath and extending distally from the position of the transducer; the distal projection comprises a catheter extension having a diameter of the order of the diameter of the catheter sheath in the region of the transducer, the projection adapted to maintain alignment of the probe with a passage of interest as the probe is moved axially for varying the view of features in the region of the passage; the distal projection comprises an elongated guide means of smaller diameter and greater flexibility than the catheter sheath; the distal projection comprises means to introduce contrast medium or other fluid distal of the probe; the elongated ultrasonic probe disposed within a lumen of a catheter sheath, the internal bore of the lumen serving to rotatably support the probe, a distal portion of the catheter sheath that corresponds with the position of the transducer being substantially transparent to acoustical energy transmitted and received by the transducer; and the probe and the sheath are cooperatively constructed and arranged to enable removal and replacement of the sheath in a disposable manner.

In preferred embodiments, the transducer comprises a single transducer element directed at an angle to the axis of the drive shaft, and there are provided means for rotating the shaft at a speed of the order of 1800 rpm, means for energizing the transducer to cause it to emit at a frequency in excess of about 15 MHz, position detecting means at the proximal end of the drive shaft for detecting the instantaneous angular position of the shaft to represent the instantaneous angular position of the transducer, and TV monitor means responsive to return signals from the transducer and the position detecting means for providing a display of an acoustical image based upon signals detected by the transducer.

In preferred embodiments, the portion of the catheter sheath which is substantially transparent to acoustical energy is integral (i.e. without a joint) with a proximal portion of the catheter sheath; the substantially transparent portion of the catheter sheath has a thinner wall than said proximal portion; and the catheter sheath comprises a resinous substance.

Another preferred embodiment comprises the elongated probe or catheter described above, in combination with a hollow trocar adapted to receive the probe or catheter, the trocar having a side-facing window adapted to register with the transducer enabling the transducer to form acoustic images of tissue into which the trocar has been forced.

Other aspects, features and advantages of the invention will be apparent from the following description of the preferred embodiments and from the claims.

The invention enables the achievement of microacoustic, close-up imaging, via catheter, of restricted regions of the body that are difficult of access.

DESCRIPTION OF THE PREFERRED EMBODIMENT

The Figures will first briefly be described.

Drawings

FIG. 2 is a side view of a disposable catheter sheath for the acoustic catheter;

FIG. 3 is a longitudinal, partially cut away view of the distal end of the rotating assembly of the acoustic catheter;

FIG. 8 is a cross-sectional view of the motor-connector assembly to which the catheter is connected while FIG. 8a is a view on an enlarged scale of a portion of FIG. 8;

FIGS. 9, 10 and 11 are graphical representations of torque in relation to angular deflection.

FIG. 12 is a block diagram of the electronic components useful with the acoustical catheter of the invention;

FIGS. 13 and 13a illustrate an acoustic imaging catheter sheath having a distal floppy guide wire;

FIGS. 14 and 14a illustrate an acoustic imaging catheter sheath having a distal anchoring needle;

FIG. 15 illustrates an acoustic imaging catheter sheath having a distal catheter extension beyond the transducer;

FIG. 16 illustrates a combination balloon dilatation-/acoustic imaging catheter sheath while FIGS. 16a, 16b and 16c illustrate stages of inflation of the balloon;

FIG. 17 illustrates an acoustic catheter sheath adapted for guidance by a guide wire;

FIG. 18 illustrates an acoustic catheter sheath which is deflectable by actuation from the proximal end;

FIGS. 19 and 19a illustrate an acoustic catheter sheath capable of injection of a fluid;

FIGS. 20 and 20a illustrate the combination of an acoustic catheter with a trocar;

FIG. 21 illustrates an integrally formed acoustic catheter sheath;

FIG. 22 illustrates an acoustic catheter sheath having an integral flexible distal extension;

General Structure

Figure 1:
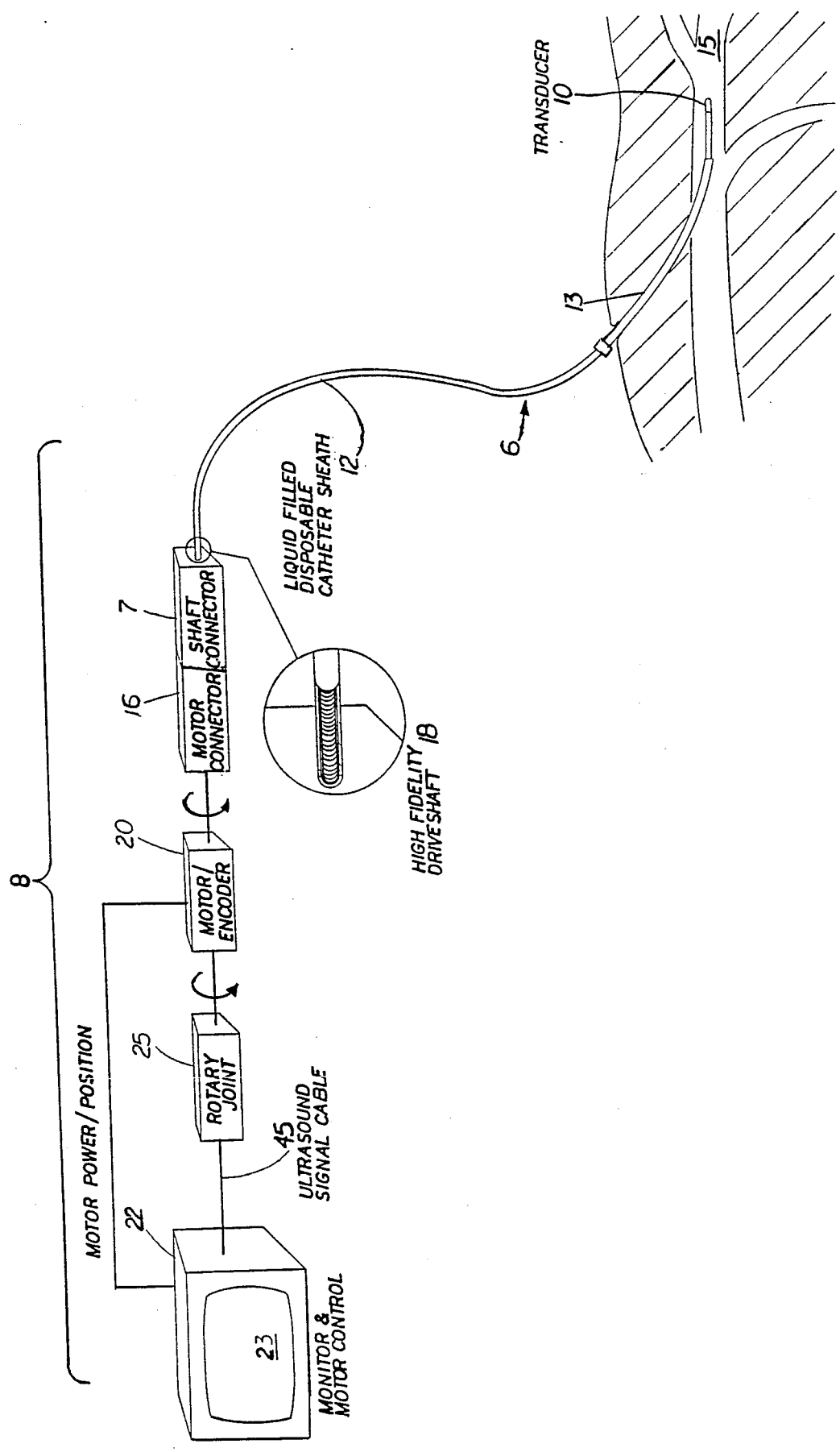
FIG. 1 is a schematic diagram of a preferred system showing use of an acoustic catheter according to the invention.

Referring to FIG. 1, a micro acoustic imaging catheter 6 according to the invention is driven and monitored by a control system 8. The catheter is comprised of a disposable catheter sheath 12 (FIGS. 2 and 4) having a sound-transparent distal window 24 provided by dome element 25, in which is disposed a miniature, rotatable ultrasonic transducer 10 (FIGS. 3 and 4) driven by a special, high fidelity flexible drive shaft 18. A relatively rigid connector 11 is joined to the proximal end of the main body of the catheter sheath, adapted to be joined to a mating connector of drive and control system 8.

The catheter is adapted to be positioned in the body by standard catheter procedures for example within a blood vessel or the heart by guiding the flexible catheter through various blood vessels along a circuitous path, starting, for example, by percutaneous introduction through an introducer sheath 13 disposed in a perforation of the femoral artery 15.

Figure 4:
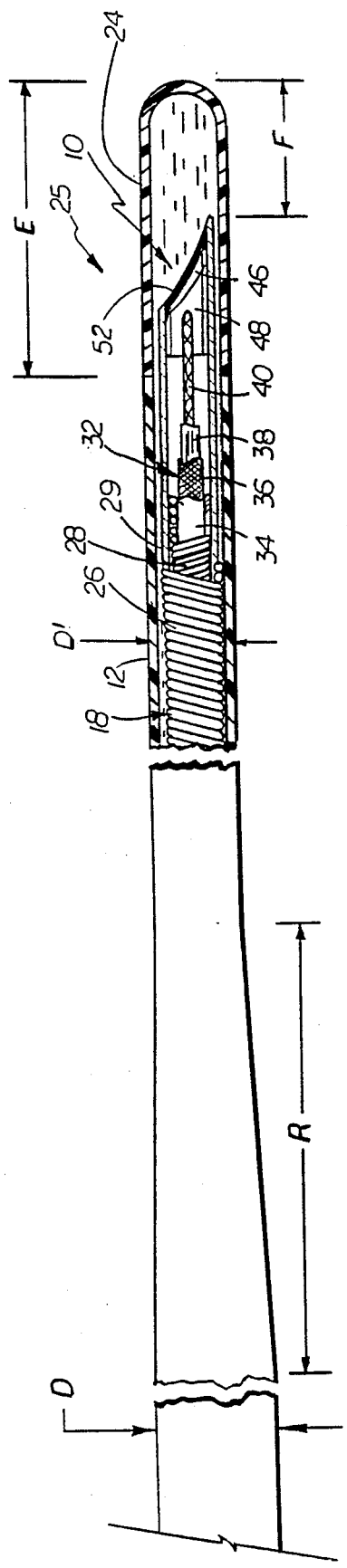
FIG. 4 is a longitudinal, cross-sectional view of the distal end of the assembled acoustic catheter.

Referring to FIG. 2, disposable catheter sheath 12 is a long tube, extruded from standard catheter materials, here nylon, e.g. with outer diameter, D, of 2 mm, wall thickness of 0.25 mm and length of 1 meter. Dome element 24, connected to the distal end of the tube, is a semi-spherically-ended cylindrical transducer cover constructed of material which is transparent to sound waves, here high impact polystyrene. This dome element has a thickness of approximately 0.125 mm and a length E of about 8 mm. For purposes described later herein, catheter sheath 12 in its distal region preferably tapers down over region R as shown in FIG. 4 to a narrowed diameter D' at its distal end, achieved by controlled heating and drawing of this portion of the original tube from which the sheath is formed. Catheter sheath 12 and acoustically transparent dome element 24, are adhesively bonded together.

Referring to FIGS. 3 and 4, the drive shaft assembly 18 is formed of a pair of closely wound multifilar coils 26, 28 wound in opposite helical directions. These coils are each formed of four circular cross-sectional wires, one of which, 30, is shown by shading. Coils 26, 28 are soldered together at both the distal and proximal ends of the assembly in interference contact, here under rotational prestress. By also providing a pitch angle of greater than about 20°, a substantial part of the stress applied to the wire filaments of the coil is compression or tension in the direction of the axis of the filaments, with attendant reduction of bending tendencies that can affect fidelity of movement. There is also provision to apply a torsional load to the distal end of the assembly to cause the drive shaft to operate in the torsionally stiff region of its torsional spring constant curve, achieved by viscous drag applied to the rotating assembly by liquid filling the narrowed distal end of the catheter sheath (FIG. 4). Such loading, together with initial tight association of the closely wound filaments in the concentric coils, provides the assembly with a particularly high torsional spring constant when twisted in a predetermined direction. Thus, despite its lateral flexibility, needed for negotiating tortuous passages, the assembly provides such a torsionally stiff and accurate drive shaft that rotary position information for the distal end can, with considerable accuracy, be derived from measurement at the proximal end of the drive shaft, enabling high quality real-time images to be produced. (Further description of the coils of the drive shaft and their condition of operation is provided below.)

Figure 5:
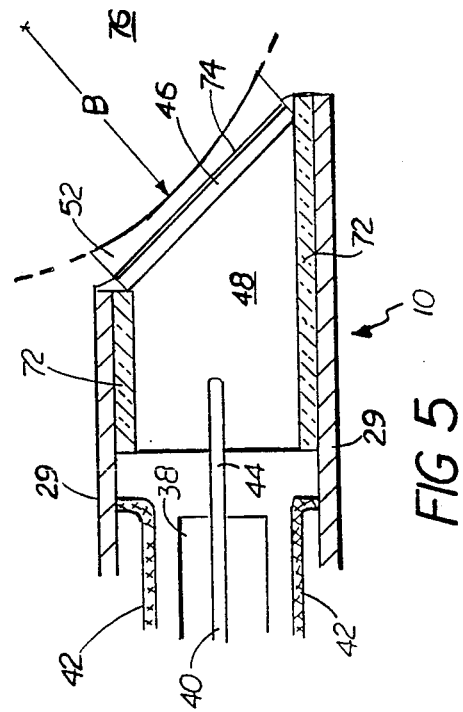
FIG. 5 is a longitudinal sectional view of the transducer element of the catheter on a greatly magnified scale.

Coaxial cable 32 within coils 26, 28 has low power loss and comprises an outer insulator layer 34, a braided shield 36, a second insulator layer 38, and a center conductor 40. Shield 36 and center conductor 40 are electrically connected by wires 42, 44 (FIG. 5) to piezoelectric crystal 46 and electrically conductive, acoustical backing 48 respectively, of the transducer. Helical coils 26, 28, especially when covered with a highly conductive metal layer, act as an additional electric shield around cable 32.

Figure 6:
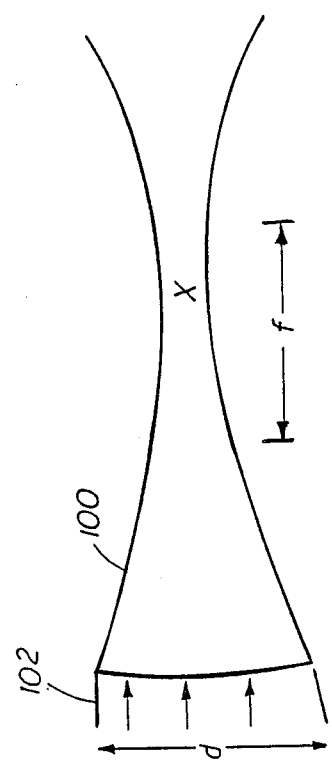
FIG. 6 is a diagrammatic representation of sound waves emanating from the acoustic lens of the catheter.

Transducer crystal 46 is formed in known manner of one of a family of ceramic materials, such as barium titanates, lead zirconate titanates, lead metaniobates, and PVDFs, that is capable of transforming pressure distortions on its surface to electrical voltages and vice versa. Transducer assembly 10 is further provided with an acoustic lens 52. The radius of curvature B of lens surface 52 is greater than about 2.5 mm, chosen to provide focus over the range f (FIG. 6) between about 2 to 7 mm. The lens is positioned at an acute angle to the longitudinal axis of the catheter so that, during rotation, it scans a conical surface from the transducing tip, the angle preferably being between 10° and 80°, e.g., 30°. Transducer backing 48 is acoustically matched to the transducer element to improve axial resolution.

The transducer assembly 10 is supported at the distal end of the drive shaft by a tubular sleeve 29 which is telescopically received over a distal extension of the inner coil 28, as shown in FIG. 3.

Referring again to FIG. 4, the length, E, of dome element 25 is sufficient to provide headroom F for longitudinal movement of transducer 10 within the dome element as catheter sheath 12 and coils 26, 28 are twisted along the blood vessels of the body. In the untwisted state, transducer 10 is a distance F, about 2 to 3 mm, from the internal end surface of the dome element 25. The dome element, along with catheter sheath 12 is adapted to be filled with lubricating and sound-transmitting fluid.

Figure 7D:
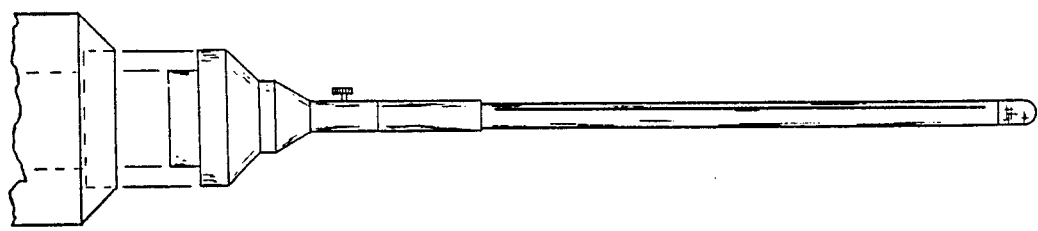
FIGS. 7 through 7d illustrate steps in filling the sheath and assembling the acoustic catheter of the figures, the syringe portions of the figures being on a reduced scale.
Figure 7C:
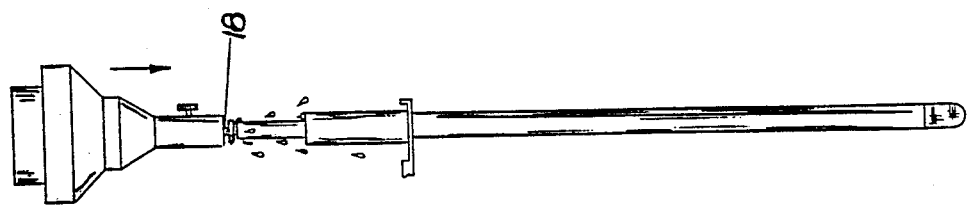
Figure 7B:
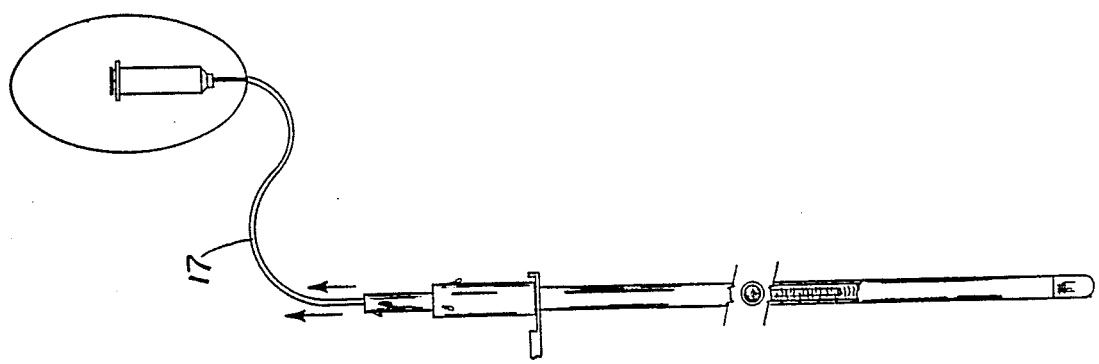
Figure 7A:
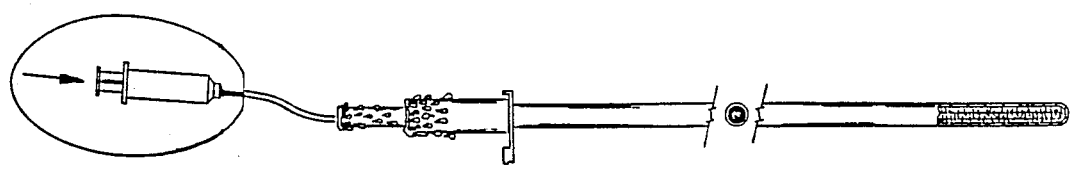
Figure 7:
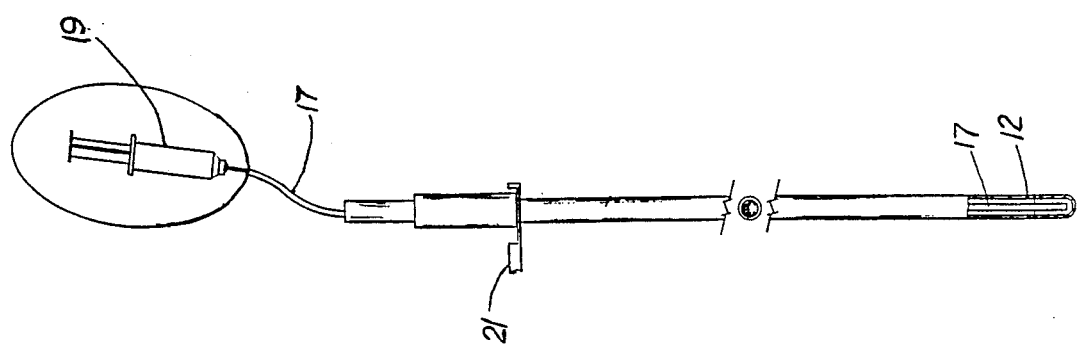

FIGS. 7–7b show the filling procedure used to prepare ultrasound catheter sheath 12 (or any of the other interchangeable sheaths, see FIGS. 13–26) for attachment to the ultrasound imaging driveshaft and transducer assembly. A sterile, flexible filling tube 17 attached to a syringe 19 is filled with sterile water. This filling catheter is inserted into the ultrasound catheter sheath 12, all the way to the distal tip. The water is then injected until it completely fills and the excess spills out of the ultrasound catheter while held in a vertical position, see FIG. 7a. This expels air from the catheter which could impair good acoustic imaging Continued pressure on the plunger of the syringe causes the flexible tube 17 to be pushed upward, out of catheter 12, FIG. 7b, leaving no air gaps behind. This eliminates the necessity to carefully withdraw the flexible filling tube at a controlled rate which could be subject to error. A holding bracket 21 is used to hold the catheter vertical during this procedure.

After the catheter sheath 12 is filled, the acoustic transducer 10 and shaft 18 are inserted, displacing water from the sheath 12, until the installed position, FIG. 7d, is achieved.

Figure 8:
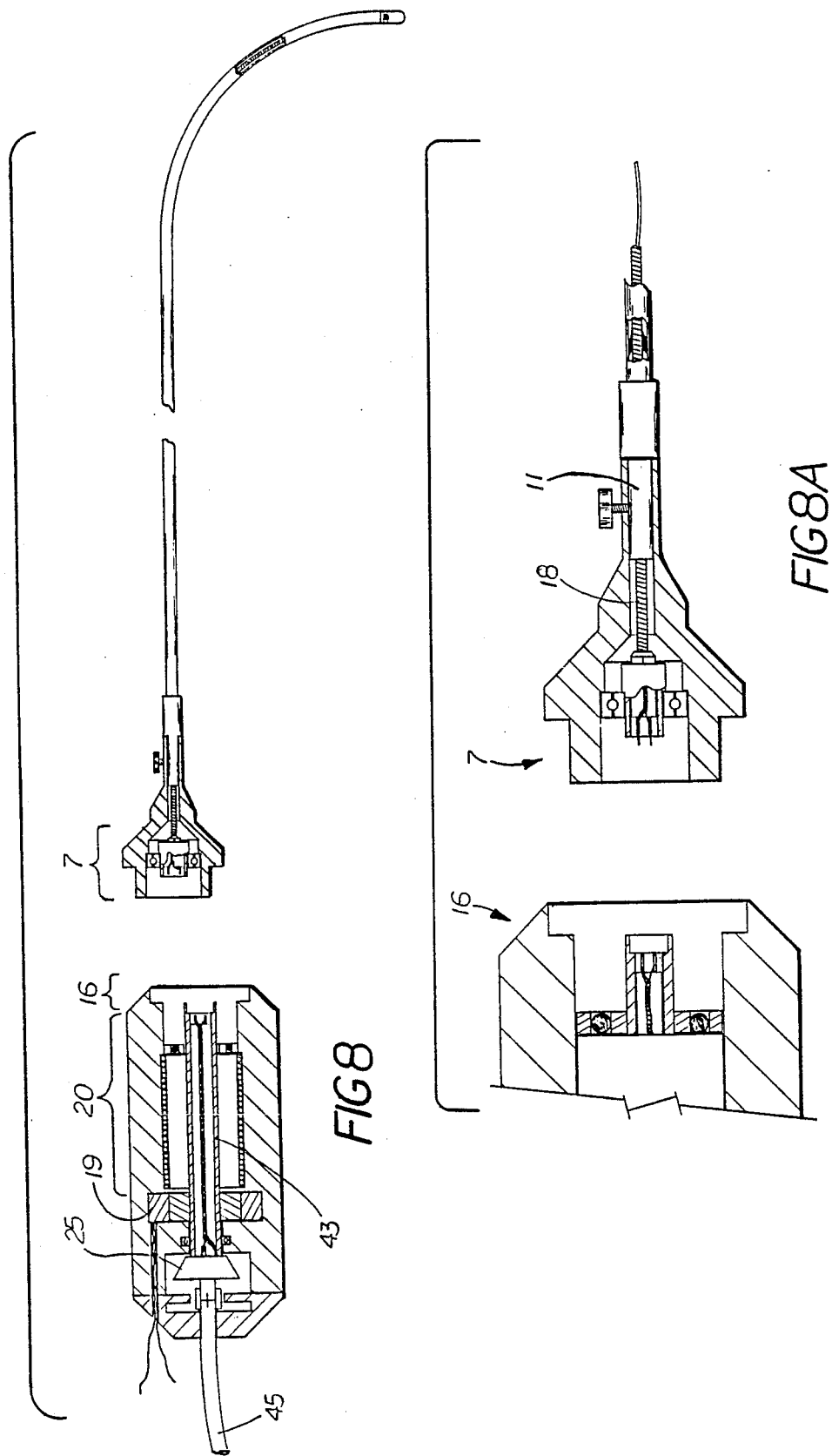

FIGS. 8 and 8a (and FIG. 1, diagrammatically) show the interconection arrangement for a connector 7 at proximal end of the acoustic catheter with connector 16 of the driving motor 20, and the path of the electric wires through the center shaft 43 of the driving motor. The center shaft and connector 16 rotate together, as do the wires that pass through the hollow motor shaft. The latter connect to a rotating electrical joint 25, which is held stationary at the back end and is connected to stationary coaxial cable 45 through a suitable connector such as a common BNC type. The enlarged view shows how the motor connector 16 and the driveshaft connector 7 mate when the two assemblies are pushed together, thereby making both electrical and mechanical contact. The catheter connector 7 is held in position by an ordinary ball bearing which provides a thrusting surface for the rotating connector 16 and driveshaft 18 while allowing free rotation. The disposable catheter sheath 12 includes an inexpensive, relatively rigid hollow bushing 11 of cylindrical construction that allows it to be slid into and held by means of a set screw in the housing that captures the non-disposable bearing, connector and driveshaft 18. Drive shaft coil assembly 18, thus attached at its proximal end to connector 16 of drive motor 20, rotates transducer 10 at speeds of about 1800 rpm. The transducer 10 is electrically connected by coaxial cable 32 extending through coil assembly 18 and via the cable through the motor to the proximal electronic components 22 which send, receive and interpret signals from the transducer. Components 22 include a cathode ray tube 23, electronic controls for the rotary repetition rate and standard ultrasonic imaging equipment, and see FIG. 12. A rotation detector, in the form of a shaft encoder shown diagrammatically at 19, detects the instantaneous rotational position of this proximal rotating assembly and applies that positional information to components 22, e.g., for use in producing the scan image.

By thus depending upon the position of proximal components to represent the instantaneous rotational position of the distal components, the rotational fidelity of the drive shaft is of great importance to this embodiment.

Manufacture and Assembly of the Drive Shaft

Referring to FIGS. 3 and 4, coils 26, 28 are each manufactured by winding four round cross-section stainless steel wires of size about 0.2 mm, so that $D_o$ is about 1.3 mm, $D_i$ is about 0.9 mm, $d_o$ is about 0.9 mm and $d_i$ is about 0.5 mm. The coils are closely wound with a pitch angle $\alpha_o$ and $\alpha_i$ where $\alpha_o$ is smaller than $\alpha_i$, e.g., 22 1/2° and 31°, respectively. (Flat wires having a cross-sectional depth of about 0.1 mm may also be used.) The pitch angles are chosen to eliminate clearances 60 between the wires and to apply a substantial part of the stress in either tension or compression along the axis of the wire filaments. The coils, connected at their ends, are adapted to be turned in the direction tending to make outer coil 26 smaller in diameter, and inner coil 28 larger. Thus the two assemblies interfere with each other and the torsional stiffness constant in this rotational direction is significantly increased (by a factor of about 6) due to the interference. Operation of the driveshaft in the torsionally stiff region with enhanced fidelity is found to be obtainable by adding a torsional load to the distal end of the rotating assembly of the catheter. The importance of rotational fidelity and details of how it is achieved warrant further discussion.

For ultrasound imaging systems, the relative position of the ultrasound transducer must be accurately known at all times so that the return signal can be plotted properly on the display. Any inaccuracy in position information will contribute to image distortion and reduced image quality. Because, in the preferred embodiment, position information is not measured at the distal tip of the catheter, but rather from the drive shaft at the proximal end, only with a torsionally stiff and true drive shaft can accurate position information and display be obtained.

Furthermore, it is recognized that any drive shaft within a catheter sheath will have a particular angular position which is naturally preferred as a result of small asymmetries. Due to this favored position, the shaft tends, during a revolution, to store and then release rotational energy, causing non uniform rotational velocity. This phenomenon is referred to as "mechanical noise" and its effect is referred to as "resultant angular infidelity" for the balance of this explanation.

According to the present invention, use is made of the fact that suitably designed concentric coils interfere with each other, as has been mentioned previously. When twisted in one direction, the outer layer will tend to expand and the inner layer contract thus resulting in a torsional spring constant which is equal only to the sum of the spring constants of each of the two shafts.

When, however, twisted in the opposite direction, the outer layer will tend to contract while the inner layer will expand. When interference occurs between the inner and outer layers the assembly will no longer allow the outer coil to contract or the inner to expand. At this point, the torsional spring constant is enhanced by the interference between the shafts and the torsional spring constant is found to become five or ten times greater than the spring constant in the "non-interference" mode.

Referring to FIG. 9, the relationship betweeen torque and angular deflection for such a coil assembly is shown, assuming one end fixed and torque applied at the opposite end. 'Y' represents mechanical noise; 'Z' resultant angular infidelity; 'T' the interference point; the slope of the line 'U', the torsional spring constant (TSC) without interference (i.e., the sum of the torsional spring constant of each of the two coils); and the slope of the line 'V', the TSC with interference. Thus, TSC is shown to increase dramatically at the interference point.

Referring to FIG. 10, by pretwisting the shafts relative to one another and locking their ends together in a preloaded assembly, the interference point is moved to be close to the rest angle and resultant angular infidelity, Z, is reduced in the given direction of rotation.

To improve upon this effect even further, dynamic frictional drag is intentionally introduced at the distal end of the shaft to raise the level of torque being continually applied to the system. This ensures operation of the shaft in the region of the high torsional spring constant or "interference" mode throughout its length, producing a rotationally stiffer shaft. This is shown in FIG. 11, where 'W' is dynamic load and 'X' is the region of operation. The use of such dynamic drag is of particular importance in certain catheters of small diameter, e.g. with outer diameter less than about 2 mm.

To form inner coil 28, four individual wires are simultaneously wound around a mandrel of about 0.5 mm outer diameter. The free ends of this coil are fixed, and then four wires are wound in opposite hand directly over this coil to form the outer coil 26. The wires are wound under moderate tension, of about 22.5 gm/wire. After winding, the coils are released. The inner mandrel, which may be tapered or stepped, or have a constant cross-sectional diameter, is then removed. The wire ends are finished by grinding. One end is then soldered or epoxied to fix the coils together for a distance of less than 3 mm. This end is held in a rigid support and the coils are then twisted sufficiently, e.g. ¼ turn, to cause the outer coil to compress and the inner coil to expand, causing the coils to interfere. The free ends are then also fixed.

The coil assembly 18 is generally formed from wires which provide a low spring index, that is, the radius of the outer coil 26 must be not more than about 2.5 to 10 times the diameter of the wires used in its construction. With a higher index, the inner coil may collapse. The multifilar nature of the coils enables a smaller diameter coil to be employed, which is of particular importance for vascular catheters and other catheters where small size is important.

After the coil assembly is completed, coaxial cable 32 is inserted within the inner coil. The cable may be silver-coated on braid 36 to enhance electrical transmission properties. It is also possible to use the inner and outer coils 26, 28 as one of the electrical conductors of this cable, e.g. by silver coating the coils.

Referring back to FIGS. 3 and 5, to form transducer 10, wire 42 is soldered to either side of electrically conducting sleeve 29 formed of stainless steel. Wire 44 is inserted into a sound absorbent backing 48 which is insulated from sleeve 29 by insulator 72. Piezoelectric element 46 of thickness about 0.1 mm is fixed to backing 48 by adhesive and electrical connection 74 is provided between its surface and the end of sleeve 29. Thus, wire 42 is electrically connected to the outer face of piezoelectric element 46, and wire 44 electrically connected to its inner face. Spherical lens 52, formed of acoustic lens materials is fixed to the outer surface of element 46.

Referring to FIGS. 4 and 7-7d, the completed drive shaft 18 and transducer 10 are inserted into disposable catheter sheath 12, positioning transducer 10 within acoustically transparent dome element 25, with liquid filling the internal open spaces. The catheter thus prepared is ready to be driven by the drive assembly, FIG. 8.

During use, rotation of drive shaft 18, due to exposure of the helical surface of the outer coil to the liquid, tends to create helical movement of the liquid toward the distal end of the sheath. This tends to create positive pressure in dome element 25 which reduces the tendency to form bubbles caused by outgassing from the various surfaces in this region.

As has been mentioned, it is beneficial to provide added drag friction at the distal end of the rotating drive shaft 18 to ensure operation in the torsionally stiff region of the torsional spring constant curve. It is found that this may be done by simply necking down the distal portion of the catheter sheath 12, as shown in FIG. 4 to provide a relatively tight clearance between the distal portion of the shaft 18 and the inner surface of the sheath, to impose the desired degree of viscous drag. As an alternative, the dynamic drag may be provided by an internal protrusion in catheter sheath 12 to create a slight internal friction against drive shaft 18.

A preferred acoustic catheter is constructed so that it may be preformed prior to use by standard methods. Thus, if the investigator wishes to pass the cathether through a known tortuous path, e.g., around the aortic arch, the catheter can be appropriately shaped prior to insertion. Such preformation can include bends of about 1 cm radius and still permit satisfactory operation of the drive shaft.

Electronics

FIG. 12 is a block diagram of the electronics of a basic analog ultrasound imaging system used with the acoustical catheter. The motor controller (D) positions the transducer B for the next scan line. The transmit pulser (A) drives the ultrasound transducer. The transducer (B) converts the electrical energy into acoustic energy and emits a sound wave. The sound wave reflects off various interfaces in the region of interest and a portion returns to the transducer. The transducer converts the acoustic energy back into electrical energy. The receiver (C) takes this waveform and gates out the transmit pulse. The remaining information is processed so that signal amplitude is converted to intensity and time from the transmit pulse is translated to distance. This brightness and distance information is fed into a vector generator/scan converter (E) which along with the position information from the motor controller converts the polar coordinates to rectangular coordinates for a standard raster monitor (F). This process is repeated many thousands of times per second.

By rotating the transducer at 1800 rpm, repeated sonic sweeps of the area around the transducer are made at repetition rate suitable for TV display, with plotting based upon the rotary positional information derived from the proximal end of the device. In this way a real time ultrasound image of a vessel or other structure can be observed.

We have found that within a blood vessel imaging system a focal point of between 1 and 7 mm is suitable and that a frequency of 15 to 40 MHz provides good resolution of vessel features in a practical manner.

Use.

As mentioned above, the acoustical imaging catheter may be introduced by standard techniques, preferably by percutaneous insertion, into any desired blood vessel. Alternatively, it can be introduced directly into a body cavity or body tissue such as an organ. Due to its rotational fidelity, the device provides a relatively high quality, real time image of blood vessel tissue and allows ready diagnosis of disease states such as occlusion or dyskinesia. The acoustic properties of various tissues can also be discerned to allow more accurate diagnosis. It is also possible to form 3-dimensional images using appropriate computer software and by moving the catheter within the blood vessel. The device is also useful in angioplasty therapy to determine the nature and geometry of intravascular protrusions. This device may be combined with existing optical devices to provide a device having an ultrasonic visualizing probe and a laser ablating ability. The device may also be used in diagnosis of, e.g., esophageal tumors or prostate carcinomas, by passing the catheter through the anus, urethra, trachea, or esophagus. The catheter is also useful for valvuloplasty by insertion through a cardiac valve. Further, in non-medical areas, the device is useful for any inaccessible passages which are fluid filled, and thus transmit sound waves.

Selectable Catheter Sheaths

A wide variety of novel disposable catheter can be substituted for catheter sheath 12 and used in the system.

FIG. 13 shows a flexible, disposable catheter sheath 12a that is constructed like sheath 12 and has, in addition at its distal tip, a floppy guide wire 80 which is useful for guiding the ultrasound device through a valve such as of the heart. The guide wire is constructed of a closely wound wire coil 82 and an internal safety wire 84 for added strength. Wire 84 is welded to the distal tip of coil wire 82 and its proximal end is bent over within dome 24 and securely anchored with epoxy cement. In another embodiment, the safety wire extends through a separate lumen of the catheter sheath to a securing point at the proximal end of the catheter. In addition to its guiding function, coil 80, with suitable variation of length and stiffness, is useful in supporting and steadying the free end of the ultrasound device during axial movement of the catheter to improve its imaging capability, see e.g. FIGS. 25–25c.

FIG. 14 shows sheath 12b having needle 86 securely anchored to the tip, useful for impaling a surface, such as that found in the interior of the heart, and temporarily anchoring and steadying the ultrasound device in a fixed position. In another embodiment, it too can have a safety wire extending to a proximal securing point. This acoustic catheter may be introduced through an introducing catheter. In another embodiment, the needle can be retracted during introduction.

FIG. 15 shows another flexible, disposable sheath 12c that is constructed so that the sonoluscent (acoustically transparent) portion 24a is spaced from the distal end instead of at the end. The extension 12x beyond the window 24a may be of the same flexible catheter material as the main body of the sheath or of a different, e.g. softer material, and may be either open, so that fluids may pass through it, or closed, so that no fluids pass through. The distal extension of the catheter sheath can serve to stabilize the lateral position of the transducer during axial movement of the catheter during imaging.

FIG. 16 shows a catheter sheath 12d on which is mounted, over the transducer area, a dilatation balloon 55 such as is commonly used for angioplasty. The balloon is adapted to be pressurized with liquid, such as water, through the same lumen that holds the ultrasound imaging device, via an inflation opening in the wall of the catheter sheath. This catheter is used to open a clogged, stenotic or narrowed passage in the body, while simultaneously measuring the progress of the dilatation procedure with the ultrasound imager. Another embodiment with a suitable balloon may be used to center or position the ultrasound device securely within a body passage or cavity and maintain its position away from a feature of interest, for instance for imaging wall of the heart. The balloon in its collapsed or unpressurized state is easily inserted prior to positioning and may be accurately positioned by use of ultrasound imaging during initial placement. In other embodiments a separate lumen is provided for inflation of the balloon and/or the balloon is spaced from the distal end of the catheter.

FIG. 17 shows sheath 12e, similar to sheath 12, which is additionally fitted with an eyelet 90 through a solid portion of the tip to allow the free passage of a guide wire 92 which is used to help guide the catheter to a region of interest inside a passage of the body.

FIG. 18 shows sheath 12f having a two lumen construction. The large lumen contains the transducer and drive shaft while the small lumen contains a wire 94. As shown, wire 94 is a deflecting wire attached near the distal end, and is free to slide through its lumen under tension applied to ring 96 to cause the catheter to bend when pulled taut, thus providing a measure of control of the orientation of the distal end of the acoustic catheter while negotiating the passages of the body or the like. In another embodiment wire 94 may be a preformed stylette, which, when inserted through the second lumen, causes deflection of the tip.

FIG. 19 shows sheath 12g having a small hole 97 at its distal end to allow the passage of a fluid under pressure, such as saline or clot dissolving enzyme such as urokinase, or radiographic contrast enhancement fluids. By this device such fluids can be introduced under precise guidance using the ultrasound imaging capability of the catheter.

FIG. 20 shows sheath 12h placed in a specially designed hollow, rigid, sharply pointed metallic trocar 98 similar to a lance, designed to be driven into the body and further into the tissue of an organ of interest, such as the liver or spleen, to provide ultrasound imaging of an area where there is no natural passageway. A side-facing window 99 in the distal region of the trocar tube allows the passage of ultrasound energy from and to the transducer to enable imaging to take place. The hollow trocar tube serves further to prevent crushing or deformation of the ultrasound catheter under the considerable pressure required to drive the device into solid body tissue. After ultrasound inspection the imaging catheter may be withdrawn from this device and a biopsy device may then be inserted in its place with the advantage that the region from which the biopsy is to be taken has been very accurately located by acoustic imaging.

FIG. 21 shows flexible, disposable sheath 12i made of integral, thin-walled extruded plastic which is more or less sonolucent. This construction avoids the necessity of having a separate dome or window attached to the distal end. The distal end is post formed (thinned, e.g. by drawing and blowing) after extrusion to provide the correct wall thickness dimension for best sonic transmission and mechanical strength and may be sealed fluid tight at the tip.

FIG. 22 shows sheath 12j which is similar to sheath 12i of FIG. 21, and additionally has an integral floppy tip made by continuing the drawing process to form a small diameter solid but flexible extension of the sheath beyond the sonoluscent area; it can achieve certain of the advantages of catheter 12a of FIG. 13 but without the additional cost of adding a separate metal floppy guide wire.

Figure 23:
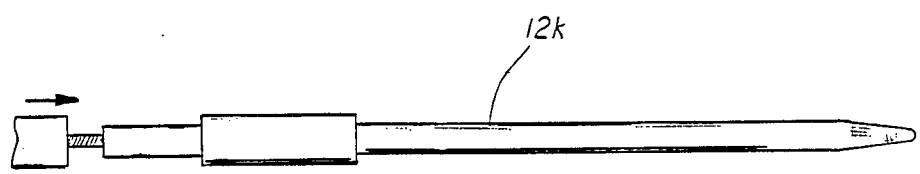
FIGS. 23 and 23a illustrate a thin-walled acoustic catheter sheath residing under tension during use.
Figure 23A:
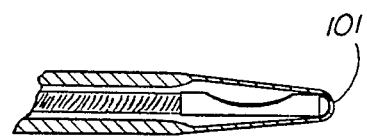

FIG. 23 shows sheath 12k which is formed to have an inner end bearing surface 101 at the distal tip for serving as an axial and radial bearing for the rotating ultrasound transducer. This bearing is e.g. a small spherical or conical formation. By applying an axial, distal thrust on the shaft, and axial proximal tension on the catheter sheath, this bearing action creates tension on the tapered area of the dome, thus maintaining its shape by stretching, and allowing an even thinner material to be used, to reduce loss of acoustic energy in the substance of the window.

Figure 24:
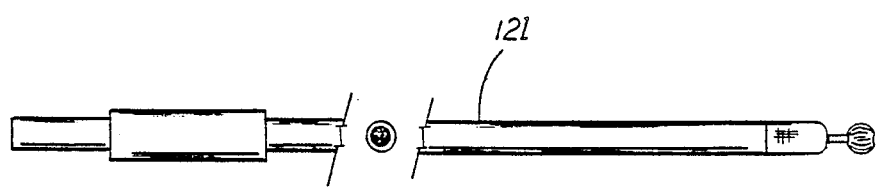
FIGS. 24 and 24a illustrate an acoustic catheter capable of driving a distal tool.
Figure 24A:
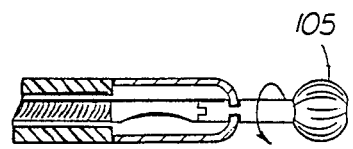

FIG. 24 shows sheath 121 which is fitted with a keyed rotating shaft that accepts the end of a similarly keyed ultrasound transducer, and acts as a power take-off for driving a rotatable instrument such as the atherectomy cutter 105, shown.

Figure 25:
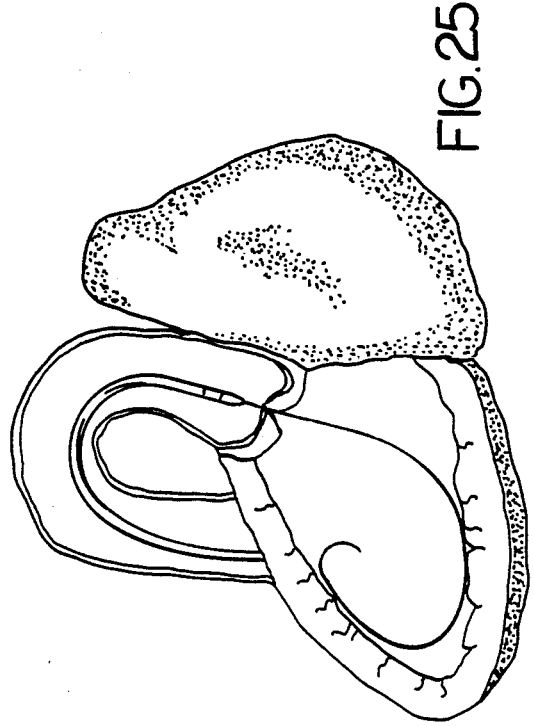
FIGS. 25 and 25a illustrate various positions of an acoustic imaging catheter during imaging of a heart valve.
Figure 25A:
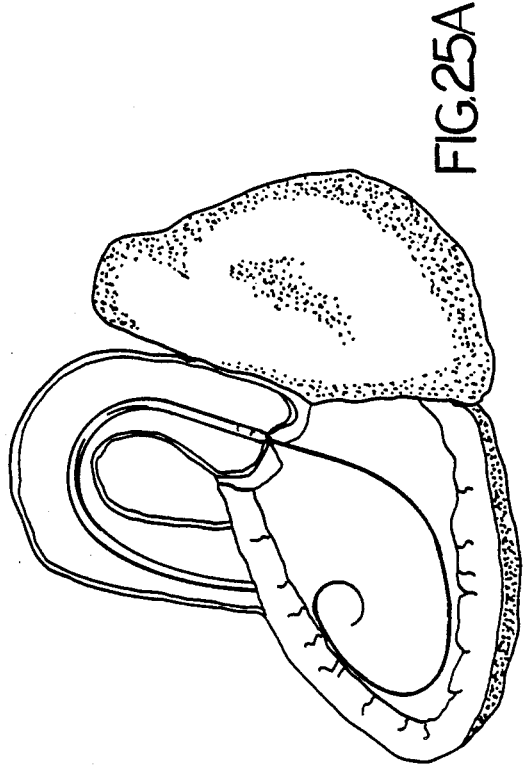
Figure 25B:
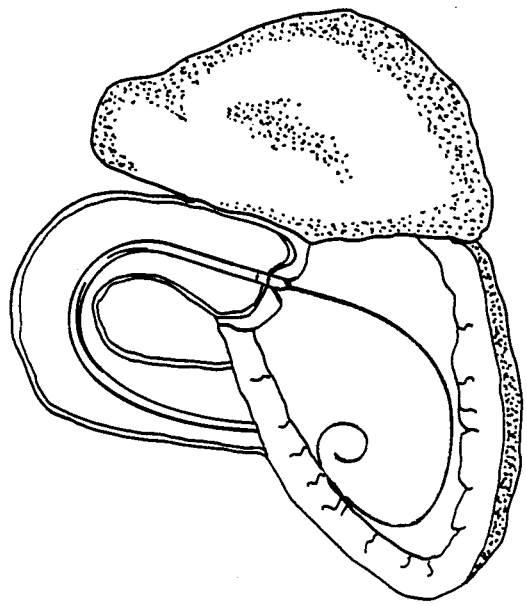
Figure 25C:
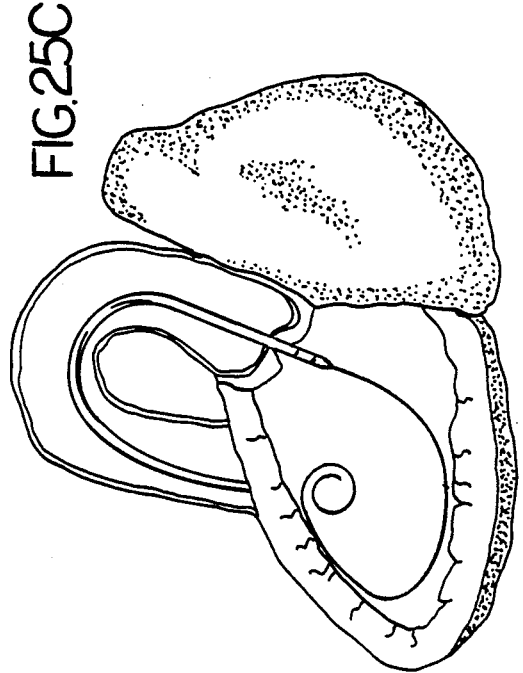

FIGS. 25-25c show a sheath constructed along the lines of sheath 12a of FIG. 13, being used in guiding and penetrating through the moving opening of a human heart valve. It shows how the floppy guiding wire acts as a stabilizer and a centering device allowing the ultrasound device to be moved forward and withdrawn repeatedly and consistently, as is desirable for proper imaging of the valve before and after valvuloplasty.

Figure 26:
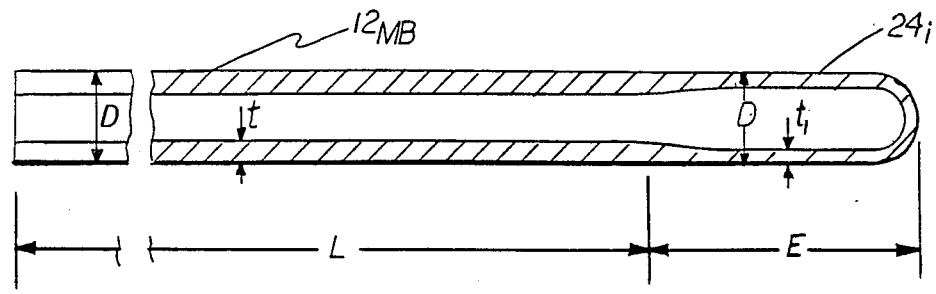
FIG. 26 illustrates an acoustic catheter sheath having an integrally formed acoustic window.

FIG. 26 shows an integrally formed catheter sheath having an acoustic window 24i originally of the same extruded material as the body of the catheter, the material of the window being modified to enhance its acoustic window properties. In this embodiment the main body $12_{mb}$ of the sheath has wall thickness t of 0.4 mm and outer diameter D of 2 mm. The integral window $24_i$ has outer diameter D corresponding to that of the main body of the catheter and a modified wall thickness $t_l$ of 0.2 mm.

Any of these catheters may be additionally fitted with radioopaque markers either at the tip or the middle or both, designed to be visible when seen under the fluoroscope while intraluminal ultrasound imaging takes place. The markers are made of a metallic material that blocks X-ray radiation or a metal filled adhesive or epoxy is applied to the surface, in a groove, or at the end of the device. Additionally the metal-filled epoxy may be used to seal the end of the device as well as provide radioopacity.

Other embodiments are within the following claims.

We claim:

1. An elongated, flexible, ultrasonic probe of the type comprising a coil-form drive shaft and an acoustic transducer head carried on the distal end of the drive shaft, wherein,
    (a) the drive shaft comprises at least a pair of inner and outer, concentric, oppositely and closely wound, multifilar coils, there being no mandrel within the innermost coil,
    (b) each coil has a ratio of outer radius of coil to thickness of coil filament in the radial direction of between about 2½ and 10,
    (c) the coils are joined together at their respective ends with interfering contact with each other along their mutual length, and
    (d) the filament of each coil have a pitch angle of about 20° or greater, so that when drive torque is applied to the drive shaft from the proximal end in the direction tending to reduce the diameter and lengthen the outer coil of a pair of said coils and increase the diameter and shorten the inner coil of said pair, a substantial component of the resultant stress on each filament of the coils is aligned with the axis of the filament,
    whereby substantial mechanical fidelity of angular displacement between the transducer and the proximal end of the drive shaft is maintained during rotation of the drive shaft,
    said acoustic transducer head having an outer diameter corresponding to the outer diameter of said drive shaft and mounted coaxially therewith, said drive shaft and transducer head forming a core that can be slidably inserted via the proximal end into a tubular sheath having a closed distal end to a directly, rotatably supported relationship with said sheath and after use can be slidably removed from said sheath for repeated re-use in other such sheaths.

2. The ultrasonic probe of claim 1 having an outer diameter throughout its length of about 2 mm or less.

3. An elongated, flexible, ultrasonic probe of the type comprising a coil-form drive shaft and an acoustic transducer head carried on the distal end of the drive shaft, wherein,
    (a) the drive shaft comprises at least a pair of inner and outer, concentric, oppositely and closely wound, multifilar coils, there being no mandrel within the innermost coil,
    (b) the coils are joined together at their respective ends with interfering contact with each other along their mutual length, and
    (c) said coils in said drive shaft being in torsionally prestressed condition, in the direction causing the outer coil of a pair of said coils to bear radially with tight contact upon the inner coil of said pair,
    said acoustic transducer head having an outer diameter corresponding to the outer diameter of said drive shaft and mounted coaxially therewith, said drive shaft and transducer head forming a core that can be slidably inserted via the proximal end into a tubular sheath having a closed distal end to a directly, rotatably supported relationship with said sheath and after use can be slidably removed from said sheath for repeated re-use in other such sheaths.

4. An elongated, flexible, ultrasonic probe of the type comprising a coil-form drive shaft and an acoustic transducer head carried on the distal end of the drive shaft, wherein,
  (a) the drive shaft comprises at least a pair of inner and outer, concentric, oppositely and closely wound, multifilar coils, there being no mandrel within the innermost coil,
  (b) the coils are joined together at their respective ends with interfering contact with each other along their mutual length, and
  (c) means at the distal end of the drive shaft adapted to apply dynamic drag to the rotation of said shaft thereby enhancing the mechanical fidelity of angular displacement between the proximal and distal ends of the probe,
  said acoustic transducer head having an outer diameter corresponding to the outer diameter of said drive shaft and mounted coaxially therewith, said drive shaft and transducer head forming a core that can be slidably inserted via the proximal end into a tubular sheath having a closed distal end to a directly, rotatably supported relationship with said sheath and after use can be slidably removed from said sheath for repeated re-use in other such sheaths.

5. The ultrasonic probe of claim 4 in combination with a disposable catheter sheath having a distal end adapted to enter the body, said sheath constructed and arranged to slidably receive said probe via the proximal end of said sheath, said sheath including a liquid-filled, relatively fixed, first sheath portion closely surrounding a segment of the distal end of the drive shaft, adapted to apply dynamic, viscous drag to said shaft during its rotation, thereby to enhance the mechanical fidelity of angular displacement between the proximal and distal ends of the probe.

6. The ultrasonic probe of claim 5 wherein said drive shaft has an outer diameter throughout its length of about 1 mm or less.

7. The ultrasonic probe of claim 5 wherein, the difference between the outer diameter of said shaft segment and the inner diameter of the corresponding sheath portion is in the range of about 0.05 to 0.15 mm.

8. The ultrasonic probe of claim 5 wherein a second sheath portion extends a substantial distance proximally from said first sheath portion, said second sheath portion being spaced a greater distance from said drive shaft than the spacing of said first sheath portion from said shaft segment.

9. An elongated, flexible, ultrasonic probe of the type comprising a coil-form drive shaft and an acoustic transducer head carried on the distal end of the drive shaft, wherein, the drive shaft comprises at least a pair of inner and outer, concentric, oppositely and closely wound, coils, said acoustic transducer head having an outer diameter corresponding to the outer diameter of said drive shaft and mounted coaxially therewith, said drive shaft and transducer head forming a core that can be slidably inserted via the proximal end into a tubular sheath having a closed distal end to a directly, rotatably supported relationship with said sheath and after use can be slidably removed from said sheath for repeated re-use in other such sheaths, in combination with a continuous liquid-confining flexible resinous tubular sheath having a closed distal end adapted to enter the body, said sheath constructed to slidably receive said probe via the proximal end of said sheath, said sheath enclosing the transducer head and drive shaft, the portion of said resinous sheath that corresponds with said drive shaft directly, rotatably supporting said drive shaft and the portion of said sheath that corresponds with the position of said transducer being substantially transparent to acoustical energy transmitted and received by said transducer, the distal portion of said sheath extending along said transducer and a supporting extent of said drive shaft having substantially constant diameter no greater than the diameter of proximal portions of said sheath.

10. The ultrasonic probe of claim 9 wherein said sheath comprises a catheter sheath having an outer diameter throughout its length of less than about 3 mm.

11. The ultrasonic probe of claim 9 wherein the outer surface of the outermost coil of said drive shaft has a liquid-pumping screw-form contour, whereby, when said drive shaft, while exposed to liquid in said sheath, is driven in the direction tending to decrease the diameter of said outermost coil, the outer surface of said coil is effective to pressurize liquid distally thereof.

12. The ultrasonic probe of claim 11 wherein there is fluid communication between the liquid-filled space along said drive shaft and the space occupied by said transducer, whereby the action of said screw-form contour of said shaft is effective to pressurize liquid in which said transducer is immersed.

13. The ultrasonic probe of claim 9 wherein said sheath comprises a catheter sheath having a distal projection supported by said catheter sheath and extending distally from the position of said transducer.

14. The ultrasonic probe of claim 13 wherein said distal projection comprises a catheter extension having a diameter of the order of the diameter of the catheter sheath in the region of said transducer, said projection adapted to maintain alignment of said probe with a passage of interest as said probe is moved axially for varying the view of features in the region of said passage.

15. The ultrasonic probe of claim 13 wherein said distal projection comprises an elongated guide means of smaller diameter and greater flexibility than said catheter sheath.

16. The ultrasonic probe of claim 13 wherein said distal projection comprises means to introduce fluid distal of said probe.

17. An acoustical imaging catheter comprising an elongated, flexible, ultrasonic probe of the type comprising a coil-form drive shaft and an acoustic transducer head carried on the distal end of the drive shaft, wherein the drive shaft comprises at least a pair of inner and outer, concentric, oppositely and closely wound, coils, said acoustic transducer head having an outer diameter corresponding to the outer diameter of said drive shaft and mounted coaxially therewith, said drive shaft and transducer head forming a core that can be slidably inserted via the proximal end into a tube having a closed distal end, said probe removably, slidably disposed within a lumen of a catheter sheath, the internal bore of said lumen serving to directly rotatably support said probe, a distal portion of said catheter sheath that corresponds with the position of said transducer head having an outer diameter no greater than that of the remainder of the catheter sheath and being substantially transparent to acoustical energy trasmitted and received by said transducer.

18. The acoustical imaging catheter of claim 17 wherein said catheter sheath has an outer diameter throughout its length of less than about 3 mm.

19. The acoustical imaging catheter of claim 17 wherein there is a distal projection supported by said catheter sheath and extending distally from the position of said transducer.

20. The acoustical imaging catheter of claim 19 wherein said distal projection comprises a catheter extension having a diameter of the order of the diameter of the catheter sheath in the region of said transducer, said projection adapted to maintain alignment of said probe with a passage of interest as said probe is moved axially for varying the view of features in the region of said passage.

21. The acoustical imaging catheter of claim 19 wherein said distal projection comprises an elongated guide means of smaller diameter and greater flexibility than said catheter sheath.

22. The acoustical imaging catheter of claim 19 wherein said distal projection comprises means to introduce fluid distal of said probe.

23. An elongated, flexible, ultrasonic probe of the type comprising a coil-form drive shaft and an acoustic transducer head carried on the distal end of the drive shaft, wherein the drive shaft comprises a pair of inner and outer, concentric, oppositely and closely wound, coils, wherein the inner coil of said drive shaft extends axially, distally from said outer coil, a tubular segment is telescopically joined to said extension of said inner coil, the outer diameter of said tubular segment being no greater than the outer diameter of said outer coil, said tubular segment protruding beyond the distal end of said drive shaft and supporting said transducer.

24. An elongated, flexible, ultrasonic probe of the type comprising a coil-form drive shaft and an acoustic transducer head carried on the distal end of the drive shaft, said acoustic transducer head having an outer diameter corresponding to the outer diameter of said drive shaft and mounted coaxially therewith, said drive shaft and transducer head forming a core that can be slidably inserted via the proximal end into a tubular sheath having a closed distal end to a directly, rotatably supported relationship with said sheath and after use can be slidably removed from said sheath for repeated re-use in other such sheaths and wherein the drive shaft comprises at least a pair of inner and outer, concentric, oppositely and closely wound, coils, the innermost coil being hollow and wherein an electric transmission line extends through said drive shaft, at least one of said coils of said drive shaft bearing a shielding-grade conductive layer to provide shielding for said transmission line.

25. An acoustical imaging catheter comprising an elongated liquid-confining catheter sheath and an elongated ultrasonic probe disposed within and rotatably supported by a lumen of said sheath, said ultrasonic probe comprising a transducer supported on the end of an elongated coil-form drive shaft, the exterior of said drive shaft exposed directly to the internal surface of said catheter lumen, the inner diameter of said lumen being no more than about ¼ mm greater than the outer diameter of said drive shaft along most of their mutual length and being no more than about 1/10 mm greater than the outer diameter of said drive shaft in the distal region of said drive shaft and said transducer, a distal portion of said catheter sheath that corresponds with the position of said transducer being substantially transparent to acoustical energy trasmitted and received by said transducer and said probe and said sheath are cooperatively constructed and arranged to enable removal and replacement of said sheath in a disposable manner, said acoustic transducer head having an outer diameter corresponding to the outer diameter of said drive shaft and mounted coaxially therewith, the exterior of said sheath being of substantially uniform diameter along said drive shaft and said transducer.

26. The acoustic catheter of claim 25 wherein
  (a) the drive shaft comprises at least a pair of inner and outer, concentric, oppositely and closely wound, hollow, multifilar coils,
  (b) each coil has a ratio of outer radius of coil to thickness of coil filament in the radial direction of between about 2½ and 10,
  (c) the filaments of each coil have a pitch angle of about 20° or greater, so that when drive torque is applied to the drive shaft from the proximal end in the direction tending to reduce the diameter and lengthen the outer coil of a pair of said coils and increase the diameter and shorten the inner coil of said pair, a substantial component of the resultant stress on each filament of the coils is aligned with the axis of the filament, whereby substantial mechanical fidelity of angular displacement between the tranducer and the proximal end of the drive shaft is maintained during rotation of the drive shaft 27. The device of any of the claim 1–8 or 26 wherein said transducer comprises a single transducer element directed at an angle to the axis of said drive shaft, means provided for rotating said shaft at a speed of the order of 1,800 rpm, means for energizing said transducer to cause it to emit at a frequency in excess of about 15 MHz, position detecting means at the proximal end of said drive shaft for detecting the instantaneous angular position of said shaft, to represent the angular instantaneous position of said transducer, and TV monitor means responsive to return signals from said transducer and said position detecting means for providing a display of an acoustical image based upon signals detected by said transducer.

28. A disposable acoustical imaging catheter sheath constructed and arranged for use with a drive and control system and adapted to receive and rotatably support a predetermined elongated ultrasonic probe of the type comprising a coil-form rotatable drive shaft of predetermined length and an acoustic transducer head carried on the distal end of the drive shaft, the path of rotation of the transducer having a diameter no greater than said drive shaft, said acoustical imaging catheter sheath comprising an elongated, liquid-confining, resinous, flexible member having a lumen for slidably receiving said probe, a distal portion of said sheath corresponding to the position of said rotatable transducer when inserted in said lumen being substantially transparent to acoustical energy transmitted and received by said transducer to provide a window therefor, the internal surface of said lumen sized to rotatably support said drive shaft, the exterior of said sheath being of substantially uniform diameter along the portion of said sheath that is constructed to receive said drive shaft and said transducer, and means at the proximal end of the catheter sheath for removably connecting it to a mating connector of said drive and control system.

29. The catheter sheath of claim 28 having a distal projection supported by said catheter sheath and extending distally therefrom.

30. The catheter sheath of claim 29 wherein said distal projection comprises a catheter sheath extension having a diameter of the order of the diameter of the catheter sheath in the region of said transducer, said projection adapted to maintain alignment of said probe with a passage of interest as said probe is moved axially for varying the view of features in the region of said passage.

31. The catheter sheath of claim 29 wherein said distal projection comprises an elongated guide means of smaller diameter and greater flexibility than said catheter sheath.

32. The catheter sheath of claim 31 wherein said catheter sheath is comprised of resinous material and said guide means comprises an integral extension of the catheter sheath.

33. The catheter sheath of claim 29 wherein said distal projection comprises means to introduce fluid distal of said probe.

34. The catheter sheath of claim 29 wherein said portion of said catheter sheath which is substantially transparent to acoustical energy is integral with a proximal portion of said catheter sheath.

35. The catheter sheath of claim 34 wherein said substantially transparent portion of said catheter sheath has a thinner wall than said proximal portion.

36. The catheter sheath of claim 28 wherein a distal portion forms an axial bearing surface adapted to be engaged under compression by said probe to maintain said sheath under tension in the region of the window.

37. The catheter sheath of claim 28 including an inflatable dilatation balloon carried on the exterior of said sheath, overlying said window.

38. The catheter sheath of claim 28 including a distal power take-off extension adapted to mount a rotatable surgical tool, said take-off extension adapted to be rotatably driven by said probe.

39. The catheter sheath of claim 28 further including an impaling means at its distal end for anchoring and steadying said catheter sheath.

40. The catheter sheath of claim 28 having a sonolucent portion spaced from the most distal end of said catheter sheath so that said distal portion can stabilize the position of said transducer during axial movement of the catheter sheath during imaging.

41. The catheter sheath of claim 28 further including at its distal end a guide eyelet slidable along a relatively stationary guidewire to enable the distal end of said sheath to slide along a pre-placed guidewire to guide the catheter in the body passage.

42. The catheter sheath of claim 28 further including a deflecting wire passing through a lumen of the sheath and attached to said sheath at its most distal end and being adapted to control the orientation of said distal end by axial displacement of said wire relative to the body of said sheath from a proximal actuating position.

43. The catheter of claim 28 wherein said sheath has an aperture at its distal end to enable passage of fluid.

44. The catheter sheath of claim 28 in combination with a hollow trocar sized to receive said catheter sheath and adapted to be driven into tissue to provide ultrasound imaging of an area where there is no natural passage way.

45. The catheter sheath of claim 28 comprised of integral, thin-walled extruded plastic which is substantially sonolucent, the distal end of said sheath being post-formed to provide a reduced wall thickness for optical sonic transmission and mechanical strength.

46. The catheter sheath of claim 28 further including an inner distal end bearing surface, said sheath arranged for axial and radial bearing of said ultrasonic probe.

47. The catheter sheath of claim 28 further including a rotatable shaft section for supporting an instrument distally thereon, said shaft section constructed to accept the end of a complementary mated drive shaft extending from said ultrasound probe, said shaft section acting as a power takeoff for driving and rotating said instrument.

48. An elongated ultrasonic probe comprising a transducer supported on the end of an elongated coil-form rotatable drive shaft in combination with a hollow-trocar adapted to receive said probe, said trocar having a side-facing window adapted to register with said transducer, while rotating, enabling said transducer to form acoustic images of tissue into which said trocar has been forced.

49. An acoustical imaging catheter constructed and arranged for use with a drive and control system, said catheter comprising, in combination, a disposable catheter sheath and an elongated ultrasonic probe of the type comprising a coil-form rotatable drive shaft of predetermined length and an acoustic transducer head carried on the distal end of the drive shaft, the path of rotation of the transducer having a diameter no greater than said drive shaft, said disposable catheter sheath adapted to receive and rotatably support said ultrasonic probe, said sheath comprising an elongated, liquid-confining, resinous, flexible member having a lumen for slidably receiving said probe, a distal portion of said sheath corresponding to the position of said rotatable transducer when inserted in said lumen being substantially transparent to acoustical energy transmitted and received by said transducer to provide a window therefor, the internal surface of said lumen sized to rotatably support said drive shaft, the exterior of said sheath being of substantially uniform diameter along said drive shaft and said transducer, and means at the proximal end of the catheter for removably connecting it to a mating connector of said drive and control system.

50. The acoustical imaging catheter of claim 49, said acoustic transducer head having an outer diameter corresponding to the outer diameter of said drive shaft and mounted coaxially therewith.

* * * * *

UNITED STATES PATENT AND TRADEMARK OFFICE
CERTIFICATE OF CORRECTION

PATENT NO. : 4,951,677

DATED : August 28, 1990

INVENTOR(S) : Robert J. Crowley, et al.

It is certified that error appears in the above-identified patent and that said Letters Patent is hereby corrected as shown below: ON TITLE PAGE:

References cited: Please insert 2,545,101 3/13/51 Meunier
2,949,910 8/23/60 Brown, et al.
3,542,014 11/24/70 Peronneau
3,749,085 7/31/73 Willson, et al.
3,749,086 7/31/73 Kline, et al.
3,773,034 11/20/73 Burns, et al.
3,779,234 12/18/73 Eggleton, et al.
3,938,502 2/17/76 Bom
4,020,829 5/3/77 Willson, et al.
4,176,662 12/4/79 Frazer
4,327,738 5/4/82 Green et al.
4,374,525 2/22/83 Baba
4,375,818 3/8/83 Sawaki, et al.
4,391,282 7/5/83 Andou, et al.
4,431,006 2/14/84 Trimmer, et al.
4,462,408 7/31/84 Silverstein
4,516,972 5/14/85 Samson
4,558,706 12/17/85 Nakada, et al.
4,572,201 2/25/86 Kondo, et al.
4,605,009 8/12/86 Pourcelot, et al.
4,674,515 6/23/87 Andou, et al.

UNITED STATES PATENT AND TRADEMARK OFFICE
CERTIFICATE OF CORRECTION

PATENT NO. : 4,951,677

DATED : August 28, 1990

INVENTOR(S) : Robert J. Crowley, et al.

It is certified that error appears in the above-identified patent and that said Letters Patent is hereby corrected as shown below:

4,794,932 1/3/89 Yock
4,732,156 3/22/88 Nakamura
4,576,177 3/18/86 Webster
4,558,706 12/17/85 Nakada, et al.
4,494,549 1/22/85 Namba, et al.
4,354,500 10/19/82 Colley
4,354,501 10/19/82 Colley
4,319,580 3/16/82 Colley
3,817,089 6/18/74 Eggleton, et al.
3,779,234 12/18/73 Eggleton, et al.
3,547,101 12/15/70 Rosauer
3,256,733 6/21/66 Carlin Foreign Patent Documents: Please insert 3,619,195 1/2/87 West Germany
2,157,828 10/30/85 United Kingdom
8,304,174 12/1983 PCT
7,814,494 11/1979 France
0,139,574 5/1985 European
0,163,502 12/1985 European

UNITED STATES PATENT AND TRADEMARK OFFICE
CERTIFICATE OF CORRECTION

PATENT NO. : 4,951,677

DATED : August 28, 1990

INVENTOR(S) : Robert J. Crowley, et al.

It is certified that error appears in the above-identified patent and that said Letters Patent is hereby corrected as shown below:

Prior Art Cited: Please insert

James S. Cole, et al., "The Pulsed Doppler Coronary Artery Catheter",
   July 1977, Vol. 56, No. 1.
Aloka Co., Ltd., Aloka Endo Scan, Model SSD-520, Urological Ultrasound
   Diagnostic System.
Bruel & Kjaer, "Diagnostic Ultrasound for Advanced Applications",
   pp. 2-15.
Olympus GF-UM2/EU-M2, Gastrofiberscope or Ultrasonic Survey/Endoscopic
   Ultrasound System, Instruction Manual, pp. 1-20.
S.S. White Industrial Products, "Rotary Motion Flexible Shafts",
   7/2/85, pp. 1-24.
Hartley, C.J., et al: "Pulsed Doppler Coronary Artery Catheter
   Transducer", Cardiovascular Ultrasonic Flowmetry: 279-298, 1985.

Column 1, line 32, after "arteries." there should be a new paragraph starting with "Other".
   Column 2, line 51, after "invention" insert a comma.
   Column 4, line 55, "Drawings" should be underlined.
   Column 5, line 48, "General Structure" should be underlined.
   Column 5, line 49, after "micro" and before "acoustic" insert a hyphen.

UNITED STATES PATENT AND TRADEMARK OFFICE
CERTIFICATE OF CORRECTION

PATENT NO. : 4,951,677

DATED : August 28, 1990

INVENTOR(S) : Robert J. Crowley, et al.

It is certified that error appears in the above-identified patent and that said Letters Patent is hereby corrected as shown below:

Column 7, line 29, after "imaging" insert a period.
Column 8, line 17, "Manufacture and Assembly of the Drive Shaft" should be underlined.
Column 10, line 48, "Electronics" should be underlined.
Column 11, line 13, "Use" should be underlined.
Column 11, line 40, "Selectable Catheter Sheaths" should be underlined.
Column 13, line 51, after "integrally" and before "formed" insert a comma.
Column 18, claim 27, line 30, delete "claim" and insert therefore -- claims --.

Signed and Sealed this

Twenty-sixth Day of May, 1992

Attest:

DOUGLAS B. COMER

Attesting Officer

Acting Commissioner of Patents and Trademarks